United States Patent [19]

Nolan et al.

[11] 4,171,253
[45] Oct. 16, 1979

[54] SELF-HUMIDIFYING POTENTIOSTATED, THREE-ELECTRODE HYDRATED SOLID POLYMER ELECTROLYTE (SPE) GAS SENSOR

[75] Inventors: Mary E. Nolan, Topsfield; Anthony B. La Conti, Lynnfield; Russell M. Dempsey, Hamilton, all of Mass.

[73] Assignee: General Electric Company, Wilmington, Mass.

[21] Appl. No.: 773,136

[22] Filed: Feb. 28, 1977

[51] Int. Cl.$^2$ .................................... G01N 27/46
[52] U.S. Cl. ........................ 204/195 S; 204/1 T
[58] Field of Search ............ 204/1 T, 1 S, 1 N, 1 K, 204/195 R, 195 S

[56] References Cited

U.S. PATENT DOCUMENTS

| | | | |
|---|---|---|---|
| 3,149,921 | 9/1964 | Warner | 204/1 T |
| 3,776,832 | 12/1973 | Oswin et al. | 204/195 R |
| 3,857,760 | 12/1974 | Breuer et al. | 204/195 S |
| 3,954,579 | 5/1976 | Cook et al. | 204/98 |

Primary Examiner—T. Tung
Attorney, Agent, or Firm—I. David Blumenfeld

[57] ABSTRACT pg,1 A compact electrochemical gas sensing cell is described for detecting gases which are either immediately dangerous to health such as carbon monoxide, $NO_2$, etc., or represent a social or public welfare risk. The latter area, for example, may require determining alcohol breath content of a driver of a motor vehicle. The cell uses a hydrated, solid polymer electrolyte which has sensing and reference electrodes positioned on one side of the solid polymer electrolyte membrane and a counter electrode positioned on the other side. One side of the hydrated SPE membrane is flooded with distilled water so that incoming gases are brought to essentially 100% relative humidity by rapid vapor phase water transport across the membrane, thereby eliminating the need for external humidification in the form of bubblers and the like. An ionically conductive hydrated SPE bridge is formed on one side of the membrane and is located spatially to provide a low resistance path between the reference and sensing electrodes.

8 Claims, 4 Drawing Figures

SELF-HUMIDIFYING POTENTIOSTATED, THREE-ELECTRODE HYDRATED SOLID POLYMER ELECTROLYTE (SPE) GAS SENSOR

The instant invention related to an electrochemical gas or vapor sensor and more particularly, to an electrochemical sensor which does not utilize a liquid electrolyte and detects gases or vapor such as carbon monoxide, $NO_2$ alcohol, etc.

Electrochemical cells to sense various gaseous constituents such as hydrogen, oxygen, carbon monoxide, etc., are known and have been described in various publications and patents. An electrochemical gas sensor may be defined as a sensor in which the gaseous constituents to be sensed are brought in contact with a catalytic electrode so that the constituent is either oxidized or reduced with the exchange of electrons. The flow of current due to the oxidation and reduction of the gaseous constituent is then a measure of the concentration of the constituent to be detected. One form of electrochemical gas sensor for gases such as hydrogen, carbon monoxide, hydrocarbons, etc., is described in an article entitled: Electrochemical Detection of $H_2$, CO and Hydrocarbons in Inert or Oxygen Atmospheres by A. G. LaConti, and H. J. R. Maget printed in the Journal of the Electrochemical Society, Volume 118 No. 3, Mar. of 1971. The electrochemical gas sensor described in the aforesaid article is one in which an electrical biasing potential is applied between the sensing and counter electrodes so that the sensing electrode is maintained at a potential which is exactly to the rest potential of a $P_t/O_2$ electrode, thus making the device insensitive to oxygen and air; consequently, the desired constituent may be sensed as it is oxidized at the electrode even though contained in an oxygen containing gas stream. In the absence of the constituent to be detected, no current flows in the external circuit because of the electrical biasing and the power consumption of the device is reduced substantially in that the cell consumes virtually no power during those intervals when the gas to be detected is not present. The electrochemical sensors described in the LaConti/Maget article were of the solid polymer electrolyte and did not use liquid electrolytes. However, as pointed out in the article, in order to maintain the potential at the sensing electrode constant so that the cell current is an accurate measure of the gas concentration, it was necessary either to maintain a hydrogen supply at the counter-reference electrode (as referred to in Col. 1 of page 507 of the article) or alternatively, the system had to be operated as a three-electrode device with the remaining electrodes operated in a potentiostatic mode. However, when the system was operated in the potentiostatic mode, either a salt bridge or sulfuric acid electrolyte bridge was required between the reference electrode and the sensing electrode in order to produce a usable and invariant output from the sensor and to alleviate potential fluctuations at the sensor electrode. The use of salt bridges or acid electrolyte bridges in the gas sensor while accomplishing the desired result of preventing potential fluctuations at the sensing electrode, introduce many difficulties if small portable sensors, particularly ones that may be small enough that may be easily carried or worn by the individual, are required. Obviously, the other approach, described in the article, namely these provisions of a separate source of hydrogen gas so as to maintain a stable hydrogen counter-reference electrode on the other side of the membrane, presents even greater difficulties from the standpoint of obtaining a small, portable device.

Another existing electrochemical gas sensor which operates in a potentiostatic mode is described in U.S. Pat. No. 3,776,832, issued Dec. 4, 1973 entitled: Electrochemical Detection Cell and in an article entitled: Controlled Potential Electrochemical Analysis of Carbon Monoxide found in a 1974 issue of American Laboratory on pages 50 et seq. The device described in these two publications is a three-electrode cell, i.e., the cell contains a sensing electrode, a counter electrode and a reference electrode. A potentiostat is coupled between the reference and the sensing electrodes to maintain the potential at the sensing electrode constant with variations at ambient or environment. This electrochemical gas sensor maintains a constant voltage at the reference electrode without the need for a source of hydrogen. This latter arrangement does, however, utilize a liquid acid electrolyte and is subject to all of the shortcomings of any electrochemical system which utilizes a liquid electrolyte, acid or alkaline. In the first instance, there is the problem of changing electrolyte concentration with time and the impact that it has on the output, sensitivity and accuracy of the device. In fact, the above cited patent points out that a liquid electrolyte reservoir must be supplied for a wick or matrix in order to maintain the concentration relatively constant. This obviously results in a large, fairly cumbersome arrangement for the sensor and one which is not very attractive from the standpoint of a portable device which may be carried or worn on a person.

In addition to changes in electrolyte concentration with time, there's always the risk of electrolyte spillage, materials corrosion, the problem of gasketing and sealing in order to prevent the electrolyte from leaking. It is also apparent that the electrode utilized in the gas sensor in the above identified patent not only functions as an oxidizing electrode, but must also act as a sealant for the liquid electrolyte. Hence, it has to be large enough, sturdy enough, etc., configuration, dimension and strength to perform this function. Utilization of a liquid electrolyte can also produce masking of active catalytic sides on the sensing electrode by electrolyte migration thereby reducing the sensitivity and output of the device.

It will be obvious from the aforesaid discussion, that electrochemical sensors of the type utilizing liquid electrolytes are inherently of the sort that makes a small portable device difficult, if not impossible, to achieve because of all of the problems and structural requirements that are associated with the use of liquid electrolytes. A need therefore exists for an electrochemical gas sensor which utilizes a hydrated solid polymer electrolyte which eliminates all liquid electrolytes and thus makes possible a much smaller device which is invariant with time, etc., and which does not require salt bridges or acid bridges between the reference and sensing electrode to enhance response and sensitivity. By the elimination of the external bridges, further reductions in size and bulk of the device become possible. Applicants have found that a sensor which uses a hydrated solid polymer electrolyte of the ion-exchange membrane type with an ionically conductive hydrated membrane bridge between the sensing and reference electrodes can be integrated into and form intrinsic part of the solid polymer electrolyte membrane itself to stable, high level output.

In addition, applicant has found that the use of a solid polymer electrolyte cation exchange membrane which exhibits rapid water vapor phase transport, the electrochemical gas sensor becomes self-humidifying. As a consequence, separate humidifying devices such as bubblers, etc., may be eliminated from the sensor again leading to a smaller, more compact and less expensive device. In addition, by eliminating independent humidifiers such as bubblers, there is essentially no chance that liquid $H_2O$ in the form of mist or droplets carried into the sensor. Where separate bubbler type saturators are used and the gas is first passed through the bubbler to bring it to a 100% relative humidity carry over of liquid $H_2O$ is obviously a possibility. Furthermore, the gas to be sensed does not contact liquid water thus minimizing the possibility of "scrubbing out" a gas such as $NO_2$, for example, which is to be sensed. By using an integrated humidifier/sensor cell, the sensor cell is maintained at essentially 100% relative humidity during operation, thus minimizing performance drop-off due to drying sensor cell SPE.

Applicant has found that this self-humidifying arrangement is possible in SPE-type gas sensor by maintaining the side of the SPE membrane away from the gas side, i.e., away from the side containing the sensing electrode flooded with distilled water. The distilled water is rapidly transported across the SPE membrane in the vapor phase rapidly bringing the incoming gases on the other side of the SPE to 100% relative humidity.

It is therefore a principal objective of this invention to provide an electrode, potentiostated electrochemical gas sensor containing an integrated ionically conductive bridge between the sensing and reference electrode.

A further objective of this invention is to provide a three-electrode, electrically biased, electrochemical gas sensor having an ionically conductive bridge between the sensing and reference electrode integrated into the solid polymer electrolyte.

Another objective of the invention is to provide a self-humidifying, potentiostated, three-electrode, electrochemical gas sensor utilizing a solid polymer electrolyte.

Still another objective of the invention is to provide a self-humidifying, electrically biased, three-electrode electrochemical gas sensor utilizing a solid polymer electrolyte.

Yet another objective of the invention is to provide a self-humidifying, electrically biased, three-electrode electrochemical gas sensor utilizing a solid polymer electrolyte with an integrated ionically conductive bridge between two of the electrodes.

Still another objectives and advantages of the invention will become apparent as the description thereof proceeds.

The various objectives and advantages of the invention are realized in an electrochemical gas sensor of the solid polymer electrolyte type in which a catalytic sensing electrode and catalytic reference electrode are positioned on one side of the membrane and a catalytic counter electrode is positioned on the other side of the membrane opposite the sensing electrode. An ionically conductive, solid polymer electrolyte bridge is provided by swelling the membrane between the counter electrode and a point which is opposite the reference electrode. This reduces the resistance between the reference and sensing electrodes, thereby maximizing the output of the device. In order to provide self-humidification and bring the gases at the sensing electrode to 100% relative humidity without the utilization of separate humidifiers of the bubbling type, the counter electrodes side of the solid polymer electrolyte is flooded with distilled water in the region of the counter electrode. By flooding one side, water in the vapor phase is transported rapidly across the membrane to the sensing electrode thereby rapidly bringing any gases in the vicinity of the sensing electrode to 100% relative humidity.

The novel features which are believed to be characteristic of this invention are set forth in the appended claims. The invention itself, however, both as to organization and mode of operation, together with further objectives and advantages thereof, are best understood by reference to the following description taken in connection with accompanying drawings in which:

Figure 1:
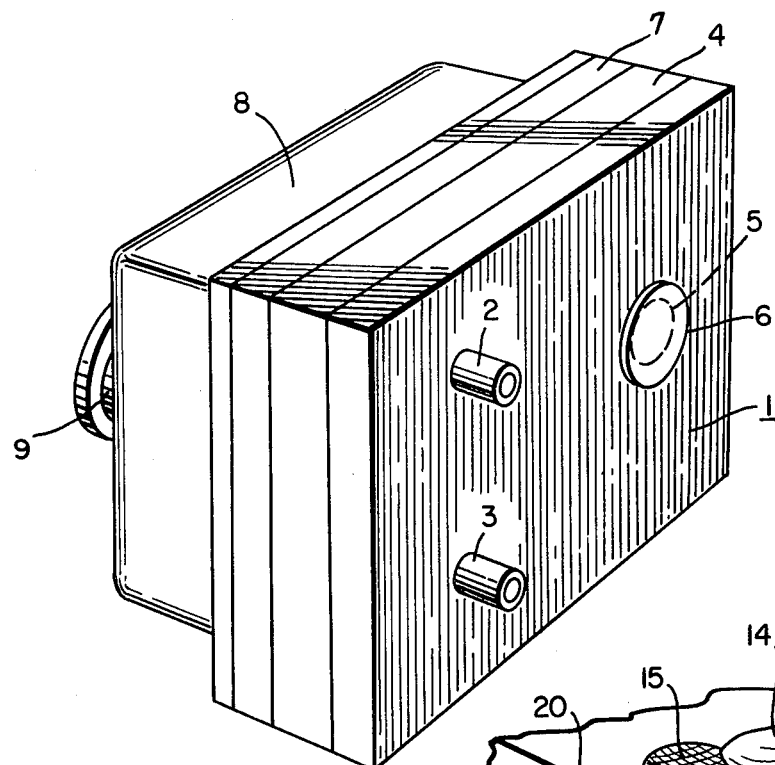
FIG. 1 is a perspective view of the cell in its assembled condition.

Operation of the electrically biased, potentiostated, three-electrode electrochemical gas sensor is based on the oxidation or reduction of the constituent to be detected at the catalytic sensing electrode. The sensing electrode is maintained at a potential to poduce rapid oxidation in the case of carbon monoxide. It is also biased at or above the rest potential of an electrode for oxygen or air so that oxidation or reduction of air has no effect on the output from the cell. The sensing electrode potential must, however, be below that at which water is dissociated to produce hydrogen and oxygen. Thus, the sensing electrode must be maintained at a potential which is much higher or more anodic than the oxidation potential of the particular gaseous constituent. For example, in the case of carbon monoxide, the electrode potential for the $CO_2/CO$ redox couple is $-0.12$ volts with reference to a $P_t/H_2$ electrode. By maintaining the reference potential in the range from 1.0 to 1.3 volts, there is rapid and immediate oxidation of the carbon monoxide reaching the sensing electrode in accordance with the following reactions at the sensing electrode and at the counter electrode:

Sensing Electrode
$$CO + H_2O = 2H^+ + CO_2 + 2e^- \qquad (1)$$

Counter Electrode
$$2H^+ + 2e^- = H_2 \text{ or} \qquad (2)$$

$$2H^+ + \tfrac{1}{2}O_2(\text{air}) + 2e^- = H_2O \qquad (3)$$

It can be seen that as the carbon monoxide is oxidized to carbon dioxide, electrons are released which flow in the external circuit and hydrogen ions are transported through the electrolyte through the counter electrode and are reduced there to form either molecular hydrogen or water. The current flowing in the external circuit as a result of this rapid oxidation of carbon monoxide to carbon dioxide is thus directly proportional to the concentration of the carbon monoxide in the gaseous stream.

Since the potential on the sensing electrode is maintained at the level which is substantially greater in the oxidizing direction, the potential required to oxidize carbon monoxide to carbon dioxide, the incoming carbon monoxide is rapidly oxidized at the sensing electrode. That is, as pointed out previously, the oxidation/reduction potential for the $CO/CO_2$ couple is $-0.12$ volts. The voltage maintained at the sensing electrode is in the range from 1.0 to 1.3 volts. It produces almost immediate and complete oxidation of the carbon monoxide. By limiting the voltage with the particular catalyst used to 1.3 volts, the potential at the sensing electrode is not sufficient to produce oxidation of water to produce hydrogen and oxygen thereby minimizing background current due to current flow produced by the oxidation of the $O_2$, $H+/H_2O$ couple. That is, the theoretical oxygen/water redox couple is at $+1.23$ volts. However, due to normal overvoltages at any sensing electrodes, the oxidation of the water will take place at some voltage greater than 1.23. With the catalytic electrode used in the instant invention which is a platinum $-5\%$ iridium catalyst of an alloy of the reduced oxides of platinum and iridium, there is no oxidation of water at 1.3 volts thereby ensuring that the current flow in the sensing cell is due exclusively to the oxidation of the incoming gaseous constituent such as carbon monoxide.

A potentiostatic circuit coupled between the reference and sensing electrodes is utilized to control the electrode potentials with the sensing electrode potential preferably maintained at 1.1 volts and the reference electrode potential at $+50$ mv below that, namely 1.05 volts. At 1.05 volts, which roughly represents the rest potential for an oxygen electrode in a hydrated SPE acid system, the oxygen in the air which contains the constituent to be sensed has no effect on the sensing device. That is, by maintaining the reference at 1.05 which is essentially the rest potential of the sensing electrode, no current flow due to the oxidation or reduction of the oxygen in the air, thus eliminating errors. Any shift of the potential at the sensing electrode affects the rate of oxidation at the electrode. That is, a drop in potential at the sensing electrode reduces the oxidation rate while a rise increases the oxidation rate. If such changes are permitted to occur, the current sensed will not be an accurate reflection of the gas concentration. Consequently, a potentiostatic circuit is provided to hold the voltage at the sensing electrode constant with reference to the hydrogen reference potential while at the same time, maintaining a potential differential between the reference and the sensing electrode to maintain good zero background current characteristics as is explained in copending application (52-EE-O-256) Ser. No. 773,012, filed Feb. 28, 1977 entitled: Zero Background Current Operation Temperature Compensated SPE Gas Detecting Cell by A. B. LaConti, et al assigned to the General Electric Company, the assignee of the present invention.

Inasmuch as the voltage at the sensing electrode and the voltage difference between the reference and sensing electrodes play such an important part in the accuracy and of the output current from the device, it is highly desirable that a good ionically conductive path is maintained between these two electrodes. That is, although ideally no current is supposed to flow between the sensing and reference electrodes in a potentiostatic mode, there are small currents that do flow between these electrodes. Since such small currents do flow, there can be a significant IR drop between these two electrodes if the resistance of the path is very high. Any such IR drop changes not only the differential voltage between these two electrodes, but may change the actual potential on the sensing electrode that produces errors in the concentration indication while differences in the voltage differential between these two electrodes may have undesirable effects on the background current at zero-air flow, also affects the accuracy of the overall indication since background current must be subtracted from the actual indication to obtain an accurate reading of the gas concentration.

In a gas sensing cell using a liquid electrolyte, both the sensing electrode and the reference electrode contact the same reservoir of electrolyte which are usually acids such as sulfuric acid or phosphoric acid. Such acid electrolyte have very low resistance, and consequently the IR drop between the reference and the sensing electrode is low. However, in cells using a solid polymer electrolyte, even though it is hydrated, the surface of the SPE membrane after assembly always has a tendency to dry out somewhat. As the surface of the membrane dries slightly, the resistance of the membrane across the dried surface can increase substantially. Hence, the resistance of the lateral path between the sensing and reference electrodes across the partially dehydrated solid-polymer electrolyte ion exchange membrane increases resulting in IR drops which introduce the errors referred to above. Applicant has found, as will be described in detail later, that the effect of membrane drying and the resulting IR drop may be substantially eliminated by forming an ionically conductive hydrated SPE bridge across the surface and through the membrane. The conductivity of the hydrated ionically conductive bridge, if positioned on the counter electrode side, plus the two paths through the membrane, is sufficiently high to reduce the IR drop between the sensing and reference electrode sufficiently to reduce variations in the sensing electrode potential and variations in the differential voltage therebetween to a minimum, thereby producing a time invariant output from the sensor, good background response.

FIG. 1 shows a perspective view of the assembled sensor, constructed in accordance with the instant invention. Thus, the gas sensor includes a bottom plate fabricated of a suitable plastic material which does not react with the gaseous constituent. Plate 1 has a pair of gas flow ports, 2 and 3, to allow a gas stream containing the constituent to be sensed, to be brought into a sensing chamber, not shown in FIG. 1, which communicates with a catalytic sensing electrode, also not shown, positioned on the near surface of a hydrated, solid-polymer electrolyte (SPE) membrane 4 which preferably is a sulfonated perfluorocarbon cation exchange membrane. Plate 1 also has an opening 5 covered by a barrier film 6 which communicates, in the preferred embodiment, with a catalytic reference electrode, not shown, positioned on the same surface of the SPE membrane tube as the catalytic sensing electrode. In order that reversibility of the air/$O_2$ electrode is optimized, the reference electrode and its active surface area should be as large as possible. The membrane area in contact with the reference area should also be fully hydrated so all of the catalyst is in contact with a highly dissociated sulfonic acid group. This permits full use of the full membrane/electrolyte area. The effective electrodes are decreased if there is:

(1) Deficiency in catalyst (as by small electrode area, low surface area, etc.).
(2) Deficiency of sulfonic acid groups (not dissociated, low IEC).
(3) Air/$O_2$ deficiency at electrode surface.

Barrier film 6 is selectively permeable to permit passage of oxygen while sufficiently blocking the gas to be sensed so that the potential of the reference electrode accurately represents the rest potential of an oxygen electrode and is not affected by the gas to be sensed. Thus, in a carbon monoxide sensor, the barrier film may be a 0.001 inch to 0.01 thick silicone film which is selectively permeable to oxygen while substantially blocking CO. Membrane 4 and bottom plate 1 are secured by means of a double-sided adhesive tape, not shown, which is positioned at all areas, but the electrodes and the openings in bottom plate 1 and, as a result, the membrane and plate, adhere firmly while at the same time blocking passage of gas between the reference and sensing electrodes. Positioned on the other side of membrane 4 is a catalytic counter electrode which is spatially oriented so to be opposite to the sensing electrode. A hydrated, ionically conductive bridge is formed between the counter electrode and a point on the other side of the membrane which is spatially oriented with the reference electrode on the near side of the membrane.

Positioned on the far side of membrane 4 is a gasket 7 which is rigidly secured to it by double-sided adhesive tape. Gasket 7, as will be pointed out in detail later, includes a pair of circular hydration ports which communicate with a reservoir 8 to maintain selected portions of the far side of the SPE membrane flooded to permit transport of water in the vapor phase across the membrane to the sensing electrode to permit humidification of the incoming gases to bring them to 100% relative humidity. The hydration ports are connected by means of a water channel which is in alignment with a ionically conductive hydrated SPE bridge on the far side of the membrane and thus maintains a continuous water contact with the surface of the swollen, hydrated membrane bridge to prevent drying out of the ionically conductive bridge.

Reservoir 8 contains a fluid filler cap shown generally at 9 which allows the introduction of distilled water which is used for flooding the far surface of the solid polymer electrolyte for self-humidification of the gases as well as for maintaining the ionically conducted hydrated SPE bridge flooded at all times.

Figure 2:
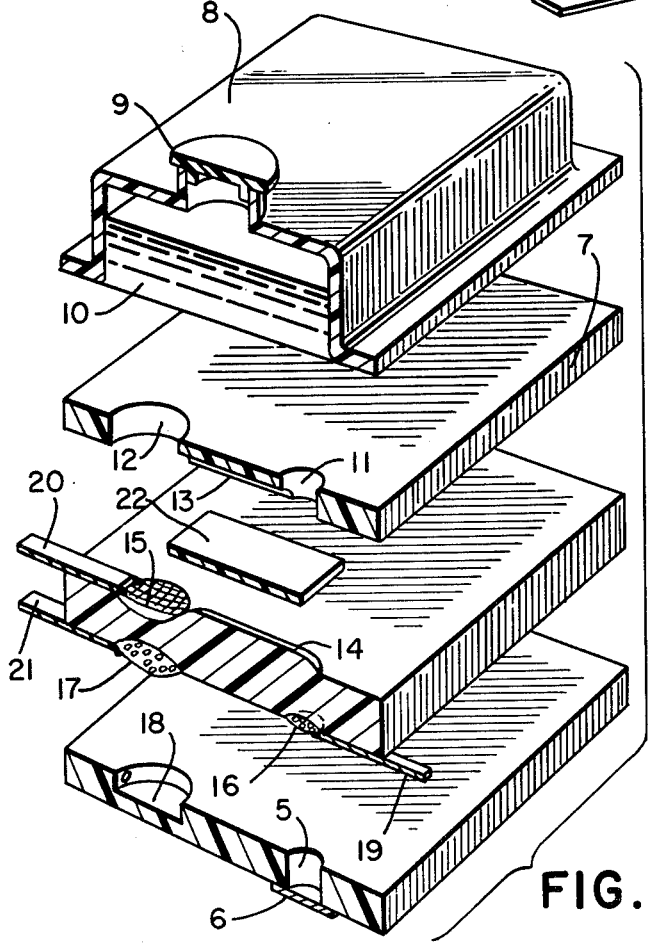
FIG. 2 is an exploded, sectional view taken along the line 2—2 of FIG. 1.

As may be seen more clearly in FIG. 2, reservoir 8 is filled with distilled water shown generally at 10 and is thus in continuous contact with the upper surface of gasket 7. Gasket 7, as pointed out below, contains a pair of hydration ports, 11 and 12, connected by means of a water channel 13 which is aligned generally to be positioned over the upper surface of a swollen, ionically conductive hydrated membrane bridge 14 on the hydrated SPE cation membrane 4. Hydration port 11 is generally aligned spatially with one end of the SPE bridge and hydration port 12 is spatially aligned with a counter electrode 15 which is bonded to and embedded in the upper surface of membrane 4. Thus, membrane bridge 14 generally extends between the counter electrode 15 to a point on the upper surface which is a spatial alignment with the catalytic reference electrode 16 bonded and embedded in the lower surface of the SPE membrane 4. The openings 11 and 12 are generally larger in area than the counter electrode and the reference electrode so that the surface of the counter electrode and in the membrane area around the electrode is flooded. As a result, water in the vapor phase diffuses rapidly through the membrane to the other side of membrane 4 particularly to sensing electrode 17 which is bonded to and embedded in the lower surface of membrane 4 and spatially in alignment with the counter electrode. Gases are brought into contact with the sensing electrode through a circular sensing port 18 in the upper surface of bottom plate 1 with the sensing port communicating through suitable channels are shown, with flow ports 2 and 3 positioned in bottom plate 1. Reference electrode 16 is in direct communication with opening 5, which is covered by the silicone barrier film 6 to pass oxygen to the reference electrode while blocking the gaseous constituents, such as CO. Each of the sensing reference and counter electrodes have suitable conductive tabs 19, 20, and 21, which may, for example, be a small tantalum wire approximately 0.012 inches in diameter spot welded to the individual electrodes. The tabs are connected to a potentiostatic circuit, presently to be described, to maintain the potentials on these electrodes constant to permit invariant, accurate operation.

A tape 22, which has adhesive on both sides, is positioned between gasket 7 and membrane 4. The tape is located on the surface of the membrane at a location away from the electrodes and the conductive, hydrated SPE bridge to fasten gasket 7 and the membrane 4 securely together. A similar tape, not shown, having adhesive on both sides is positioned between the lower surface of membrane 4 and the top side of bottom plate 1. The tape is located between electrodes 16 and 17 to secure the membranes to the bottom plate and to block flow of the gases between the reference and sensing electrodes. Reservoir chamber 8 is securely fastened to gasket 7 by means of a suitable adhesive tape located between flange portion of the reservoir housing and the edges of gasket 7, thereby securing the housing firmly against gasket 7 and sealing it against leakage.

Figure 3:
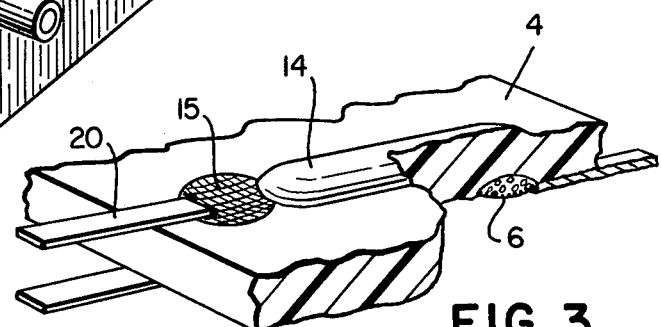
FIG. 3 is a partially broken away view of the solid polymer of FIG. 2 electrolyte showing the ionically conducted bridge on one side of the polymer etc.

FIG. 3 is a partially broken away perspective view of SPE membrane 4 and shows the hydrated bridge as well as the reference electrode on the bottom surface of the membrane. Thus, it may be seen that counter electrode 15 is bonded to and embedded into the upper surface of the membrane and a conducting tab 20 is attached to the counter electrode by spot welding or the like. The catalytic electrode, as will be described in detail later, is a bonded mass of particles of a platinum-5% iridium alloy catalyst and hydrophobic particles such as polytetrafluoroethylene (a material sold by duPont Company under its trade designation, Telfon). The bonded mass of catalytic material and hydrophobic particles is supported in a metallic, current conducting screen which is then bonded to and embedded in the surface of the membrane. The membrane is swollen to produce a hydrated ionically conductive SPE bridge 14 which extends from counter electrode 15 along the lateral surface of the membrane and through the membrane to a position which is spatially aligned with reference electrode 16 which is bonded to and embedded in the lower surface of membrane 4. Thus, there is a good ionically conducting path from the sensing electrode 17, not shown in FIG. 3, (which is spatially aligned with counter electrode 15) through the membrane to reference electrode 16. This low resistance, and highly ionically conductive path between the reference and the sensing electrodes thereby substantially eliminates or minimizes IR drops between the sensing and reference electrodes which are likely to introduce changes in the potential at the sensing electrode as well as changes in the differential voltage to be maintained between the sensing and referencing electrodes; changes which introduce undesirable errors into the operation of the device.

Hydrated SPE Exchange Membrane

The solid polymer electrolyte ion-exchange-membrane 4 which separates the sensing electrode from the counter electrode, is characterized by ion transport selectivity. Being a cation exchange membrane, it permits passage of positively charged ions, i.e., cations, and rejects and blocks passage of negatively charged ions, i.e., anions. Thus, the hydrogen ions produced through the oxidation of the carbon monoxide at the sensing electrodes are transported through the ion-exchange-membrane to the counter electrodes where it is reduced by the addition of electrons to produce molecular hydrogen or reacts with $O_2$ (air) to form water. There are various classes of ion exchange resins which may be fabricated into membranes to provide selective transport of cations. Two broad classes are the so-called sulfonic acid cation exchange resins and carboxylic cation exchange resins. In the sulfonic acid membranes, the ion exchange groups are hydrated sulfonic acid radicals (i.e., $SO_3H^+ \cdot XH_2O$) which are attached to a polymer backbone by sulfonation. In the carboxylic resins, the ion exchanging group is $-COOH$. The ion exchanging acid radicals in both classes are fixedly attached to the backbone of the polymer by sulfonation and otherwise and thus provide ion exchange capacity. The concentration of the electrolyte, however, remains fixed since the electrolyte, i.e., the acid radical, is attached to the polymer backbone and is not mobile within the membrane. While cation exchange membranes of either kind may be utilized in the invention, the sulfonated polymer type is preferred. There are many types of sulfonated polymer exchange resins. However, the perfluorocarbon sulfonic acid membranes are preferred because they not only provide excellent cation transport, but they are also highly stable, are not affected by acids and strong oxidants, and have excellent thermal stability. In addition to these highly desirable chemical and physical properties, they are further characterized by the fact that they are essentially invariant with time and thus do not degrade. A preferred cation polymer membrane is one in which the polymer is a hydrated copolymer of polytetrafluoroethylene (PTFE) and polysulfonyl fluoride vinyl ether containing pendant sulfonic $(SO_3)$ acid groups. The sulfonic groups are chemically bound to the perfluorocarbon backbone. The membrane is hydrated by soaking it in 100° C. water for 30 minutes. This yields a membrane having 30% to 40% water based on dry weight of membrane. The water content remains invariant providing the membrane is not allowed to dry out. The structure of the sulfonated perfluorocarbon is as follows:

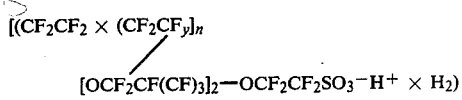

The ionic conductivity is provided by the mobility of the hydrated hydrogen ions ($H^+ \cdot XH_2O$). Electrodes 15, 16 and 17 are in the form of a decal mounted in a titanium screen and are integrally bonded to and embedded in the surface of the polymeric cation exchange membrane. One process for doing so is described in detail in U.S. Pat. No. 3,134,697, entitled "Fuel Cell," issued May 26, 1964 in the name of L. W. Niedrach and assigned to the General Electric Company, the assignee of the instant application. Briefly speaking, the electrode structure is forced into the surface of a perfluorocarbon ion-exchange-membrane, thereby integrally bonding the gas absorbing hydrophobic particle catalyst mixture to and embedding it in the surface of the ion-exchange resin membrane.

The membrane is equilibrated by immersing it in boiling water, i.e., 100° C. to produce a hydrated SPE ion-exchange-membrane. Thereafter, the membrane is further processed to form the ionically conductive hydrated SPE bridge 14 over a selected portion of the membrane. To this end, the membrane is further hydrated by an "in situ" addition of boiling water (three additions, ten minutes apart). That is, boiling water is poured in and allowed to pass through the hydration ports into the water channel 13. The water swells the area underneath the hydration channel which extends between the counter electrode and the spatial projection of the reference electrode on the lower surface of the membrane. Exposure to the boiling water produces a swelling of the surface underneath the water channel to produce the bridge which is thus hydrated to produce a good ionically conductive path. This procedure is repeated three times, ten minutes apart, thereby producing the hydrated bridge 14.

As was pointed out previously, the gas sensor described in the instant application is a self-humidifying arrangement in which water transport across the membrane is achieved by transporting water across the membrane to the sensing electrode to bring the incoming gases to 100% relative humidity.

In order to obtain the maximum transport of water in the vapor phase across the membrane, the SPE membrane should have the highest possible water content, i.e., the highest possible ion exchange capacity (IEC). The ion exchange capacity and hence the water content of the membrane is controlled by making the meq/gram of dry membrane as high as possible. Thus, for a sulfonated perfluorocarbon membrane of the type sold by duPont by their trade designation Nafion, excellent water vapor transport will be achieved whenever the membrane has an meq/gram of dry membrane is in the range 0.83 to 0.95.

Catalytic Electrodes

The cell electrodes are gas permeable, noble metal alloy catalytic electrodes comprising noble metal alloy particles bonded to particles of a hydrophobic polymer such as polytetrafluoroethylene. The catalytic electrodes are preferably a bonded mixture of reduced oxides of a platinum-5% iridium to platinum 15% iridium alloy and of PTFE hydrophobic particles. The manner of fabricating the reduced oxides of platinum-iridium are described in detail in U.S. Pat. No. 3,992,271, Ivan F. Danzig, et al, issued Nov. 16, 1976 and assigned to the General Electric Company, the assignee of the present application. The nature and character of an electrode comprising a mixture of particles of a gas-absorbing noble metal bonded with particles of hydrophobic material such as polytetrafluoroethylene and process for fabricating the same is described in detail in U.S. Pat. No. 3,432,355, entitled "Polytetrafluoroethylene Coated and Bonded Cell Structure" issued Mar. 11, 1969 in the name of L. W. Niedrach, et al and assigned to the General Electric Company, the assignee of the present application and in U.S. Pat. No. 3,297,484, entitled "Electrode Structure and Fuel Incorporating the Same" issued Jan. 10, 1967 in the name of L. W. Niedrach which is also assigned to the General Electric Company, the assignee of the present invention.

As pointed out in U.S. Pat. No. 3,992,271, the Platinum-5% Iridium catalyst which consists of reduced oxides of the Platinum Iridium alloy is prepared by thermally decomposing mixed metal salts of the elements of the alloy. The actual method of preparation is a modification of the Adams method of platinum preparation by the inclusion of a thermally decomposable iridium halide such as iridium chloride. In one example of the method finely divided halide salts of platinum and iridium are mixed in the same eight ratio of platinum iridium as is desired in the final alloy. An excess of sodium is incorporated in the mixture fused in a silica dish at 500° C. for three hours. The residue is then thoroughly washed to remove the nitrates and halides present. The resulting suspension of mixed oxides is reduced at room temperature by using an electrochemical reduction technique. The product is dried thoroughly aand ground and sieved through a mesh nylon screen. The reduced oxide of platinum-5% iridium alloy thus produced is then bonded with the hydrophobic polytetrafluoroethylene particles in accordance with the procedure described in Niedrach, U.S. Pat. No. 3,432,355 referred to above and bonded and embedded into the surface of the membrane by the process described in U.S. Pat. No. 3,134,697 above.

Figure 4:
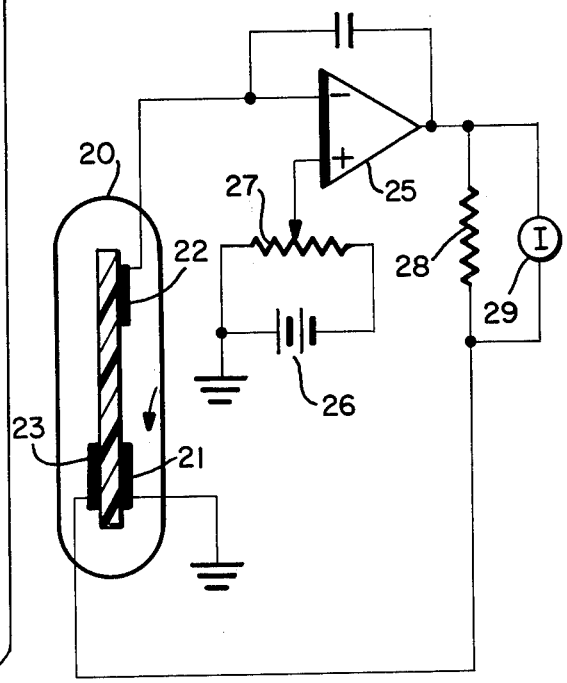
FIG. 4 is a schematic diagram showing the gas sensing cell and a potentiostatic circuit for controlling operation of the cell and maintaining the reference and sensing electrodes at a desired potential.

FIG. 4 illustrates schematically an arrangement in which the electrodes of an SPE-type gas sensor are coupled to a potentiostatic circuit which maintains the potential at the sensing electrode constant at the desired level and maintains the proper potential difference between the sensing and the reference electrodes. Potentiostatic devices are well known in the art and only a brief description thereof will be provided in connection with FIG. 4 for the sake of completeness. Thus, the SPE sensing cell is shown at 20 and includes a solid polymer electrolyte ion exchange membrane having sensing electrode 21, a reference electrode 22 on one side of the membrane, and a counter electrode 23 at the other side. The reference electrode 22 is coupled to the inverting input terminal of an operational amplifier 25 and is compared to a reference voltage from a DC supply source 24 which is applied to the non-inverting input of amplifier 25. DC source 24 includes a battery or other power source 26, the positive terminal of which is grounded. Potentiometer resistor 27 is connected across battery 26 and has a slider which is connected to the non-inverting terminal. The position of this slider is so adjusted to represent the potential at which the sensing electrode is to be maintained. Thus, in the case of a carbon monoxide sensor, reference electrode 22 is maintained at 50 mv below the sensing electrode potential so that the reference voltage at potentiometer resistor 27 is maintained at one 1-1 volts. With a voltage differential of +50 mv between the sensing and reference electrode, the sensing electrode is maintained at 1.1 volts with respect to a platinum/$H_2$ electrode. The potentiostatic circuit thus shown in FIG. 4 senses any change in the voltage between the reference and sensing electrode and compares it to the preset value at the potentiometer slider. Any changes are used to generate a current at the output of operational amplifier 25 between counter electrode 23 and sensing electrode 21 to eliminate the difference voltage producing it. The output current is sensed across resistor 28 by a suitable meter 29.

The current required to drive the system back to null balance is representative of the concentration of the gas being sensed. That is, as a gas such as carbon monoxide is oxidized to $CO_2$ and the electrons are liberated by the potential at the sensing electrode tends to shift as does the differential voltage. A current is generated to drive the system through a negative feedback mode back to its null point, namely to maintain the sensing electrode at 1.1 volt and the differential voltage between the reference and sensing voltage at +50 mv. The current required to do so is then a direct indication of the gas concentration since it is the oxidation of the gas which has produced the change in the differential voltage which requires a shift in the current to drive the system back to null balance.

As has been pointed out previously, the voltage range at the sensing electrode with respect to a platinum/hydrogen reference electrode is between 1.0 volts and 1.3 volts with the preferred voltage being 1.1 volts. The upper voltage is limited to a maximum of 1.3 to avoid oxidation of the water since this water reaction competes with the oxidation of the carbon monoxide and introduces current flow which produces errors in the sensing of the gas concentration. The voltage should not be allowed to go below 1.0 volts in order to maintain an oxide coating on the surface of the catalytic sensing electrode. That is, at 1.0 volts or above the platinum-5% iridium reduced oxide alloy has a thin oxide film on the surface which enhances operation and also prevents carbon monoxide poisoning of the catalyst. Below 1.0 volts, the oxide at the surface of the catalyst is removed and there is a risk of the carbon monoxide poisoning the catalyst. In addition, there is a possibility of reducing oxygen, thus introducing a competing reaction which produces a current flow which introduces an error factor into the measurement of the gas concentration. That is, any current flow which is due to anything but the oxidation of carbon monoxide, as for example, by reduction of oxygen or oxidation of water, which are competing reactions, introduce errors.

In order to illustrate the manner in which an ionically conductive bridge integral with the SPE membrane results in improved performance, electrode sensor cells were fabricated and tested in the following fashion. A cell was built in which Teflon bonded platinum-5% iridium electrodes were bonded to a sulfonated fluorocarbon membrane. Sensing and counter electrodes were approximately 11/16ths inch in diameter and the reference electrode approximately 5/16ths inch in diameter. The sensing and reference electrodes were on the same side of the solid polymer electrode. Tantalum wires of approximately 0.012 of an inch were spot welded to the electrodes for current collection. The counter electrode side was flooded with 10 cc distilled water at ambient temperature through the use of a gasket having hydration ports. The cell, however, did not have a hydrated membrane bridge. The cell was activated using a potentiostatic circuit. The sensing electrode was maintained at 1.1 volts +50 mv above the reference electrode. Testing was conducted by exposing the reference electrodes to ambient air and the sensing electrode to an 18 parts per million carbon monoxide in air feed. The resulsts were as follows:

| Total Signal ($\mu$A) With 17 ppm CO | Background Signal ($\mu$A) Due to Air | Sensor Output ($\mu$A) Due to CO Alone | Reservoir Solution |
|---|---|---|---|
| +4 to 6 | +2 | 4 | Distilled H$_2$O |
| +5 to 6 | +2 | 4 | " |
| Add boiling distilled H$_2$O and then allow to cool to 25° C. | | | |
| −4 to −5 | 2 | 4 | " |

The cell assembly was then modified by the addition of liquid electrolytes such as sulfuric acid at various concentrations to rhe reservoir side and the output measured again with an 18 part per million concentration of carbon monoxide in air stream. The output date for the cell was as follows:

| Total Signal ($\mu$A) With 18 ppm CO | Background Signal ($\mu$A) Due to Air | Sensor Output ($\mu$A) Due to CO Alone | Reservoir Solution |
|---|---|---|---|
| +10 to 12 | +2 | +10 | 0.1 NH$_2$ SO$_4$ |
| 14 | +1 | +13 | .5 NH$_2$ SO$_4$ |
| +18 to 20 | NIL | +20 | 1.0 NH$_2$ SO$_4$ |
| +22 to 24 | +2 | +22 | 1.5 NH$_2$ SO$_4$ |

The data indicates that a liquid electrolyte bridge between the sensing and the reference electrode increases magnitude of response. However, by adding liquid electrolyte, it becomes difficult to maintain the cell output invariant as the electrolyte concentration changes with time. The danger of acid spillage and migration of electrolyte to cover catalytic sites is also still present.

The sensor cell was disassembled and a small water channel of the type shown in FIG. 2 was inserted in the gasket with the water channel extending between the counter electrode and a spot on the surface of the membrane which was in spatial alignment with the reference electrode on the other side of the membrane. The entire SPE membrane was boiled in distilled water prior to assembly to hydrate it. The cell was then exposed to an air stream containing 18 parts per million of carbon monoxide. A liquid electrolyte in the form of 1.5 normal sulfuric acid solution was added to the reservoir side and the sensor output measured. The results were as follows:

| Total Signal ($\mu$A) With 18 ppm CO | Background Signal ($\mu$A) Due to Air | Sensor Output ($\mu$A) Due to CO Alone | Reservoir Solution |
|---|---|---|---|
| +12 | +2 | +10 | Distilled H$_2$) |
| +24 | +2 | +20 | 1.5 NH$_2$SO$_4$ |

It can be seen that the partially hydrated bridge formed due to the addition of boiling distilled water does increase the sensitivity of the gas sensor from 4 to 10 microamps for an 18 ppm concentration, but it is still substantially below the cell output for the same gas concentration, but utilizing a 1.5 N sulfuric acid liquid electrolyte bridge.

Thereafter, the SPE membrane was further hydrated along a selected portion of the membrane, i.e., in the bridge area, by "in situ" addition of boiling water (three additions—10 minutes apart). The sensor was allowed to cool to 25° C. and then retested with an 18 ppm CO concentration in air. The output of the sensor with the counter side flooded by distilled was as follows:

| Time | Total Signal ($\mu$A) With) 18 PPM CO | Background Signal ($\mu$A) Due to Air | Sensor Output ($\mu$A) Due to CO Alone | Reservoir Solution |
|---|---|---|---|---|
| 0800 | 23–24 | 2 | 22 | Distilled H$_2$O |
| 1200 | 24 | 2 | 22 | " |
| 1745 | 23 | 2 | 21 | " |

It is apparent from this data that the hydrated SPE bridge formed by "in situ" addition of boiling water to the reservoir increases the output signal and also maintains it invariant with time. The output of the cell with an integrated SPE bridge is equal to the produced by a sensor in which a liquid electrolyte bridge while eliminating all of the problems normally associated with the use of liquid electrolytes The same cell was used to detect NO in an air feed at 30 cc/min at various concentrations with the following results:

| NO Conc (ppm) | Signal ($\mu$A) |
|---|---|
| 20 | 38 |
| 30 | 53–54 |
| 41 | 74–75 |

It is apparent from this data that NO may be detected at low concentrations in the same fashion as CO and that good sensor output in range 1.5–2 $\mu$A/ppm is obtained with this cell construction.

It is therefore apparent that an improved, compact gas sensor has been provided which utilizes a solid polymer electrolyte having an integral ionically conductive bridge between a reference and sensing electrodes which is not subject to all of the shortcomings normally associated with potentiostated, three electrode, gas sensors utilizing liquid electrolytes.

While embodiments of this invention have been shown and described, it will, of course, be understood that the invention is not limited thereto, since many other arrangements both in the devices and structures and in the process steps may be employed. It is contemplated by the appended claims to cover any such modifications that fall within the true scope and spirit of this invention.

What is claimed as new and desired to be secured by Letters Patent of the United States is:

1. In an electrochemical gas-sensing device for detecting the concentration of a selected gaseous constituent in a carrier gas stream, the combination comprising:
    (a) an ion transporting membrane;
    (b) catalytic sensing and reference electrodes positioned on one side of the membrane and a counter electrode positioned on the opposite side of said membrane;
    (c) potentiostatic circuiting coupling the sensing, reference and counter electrodes for maintaining the potential at the sensing electrode constant and for maintaining a fixed potential difference between sensing and reference electrodes by driving current between the counter and sensing electrodes through said ion transporting membrane, said sensing electrode being maintained at a potential which makes the device insensitive to the carrier gas;
    (d) an ionically conductive, low-resistance path on one side of the membrane, said path extending between the counter electrode and an area which is spatially aligned with the reference electrode, said membrane having been treated to provide said low-resistance path between the counter electrode and an area spatially aligned with said reference electrode;

(e) means for exposing the sensing electrodes to a carrier gas stream containing the gaseous constituent to be sensed;

(f) means for measuring the current which flows between the counter and sensing electrodes to maintain the sensing potential constant, said current being a measure of the gas concentration.

2. The electrochemical gas sensing device according to claim 1 wherein each of said catalytic electrodes comprises a mixture of noble metal catalyst particles and hydrophobic particles bonded to and embedded in said membrane.

3. The electrochemical gas sensing device according to claim 1 wherein said reference electrode is exposed to an air stream which does not contain the gaseous constituent to be sensed.

4. The electrochemical gas sensing device according to claim 1 wherein said sensing and counter electrodes are spatially aligned on opposite sides of the said membrane.

5. The self humidifying gas sensing device according to claim 4 including an ionically conductive solid polymer electrolyte bridge integral with said membrane and located between the sensing and reference electrodes.

6. The self humidifying gas sensing device according to claim 4 wherein each of said electrodes comprises a mixture of noble metal catalyst particles and hydrophobic particles.

7. The self humidifying gas sensing device according to claim 4 wherein said electrodes are bonded to and embedded in the ion-exchange membrane and the carrier gas stream is air.

8. In a self humidifying, electrochemical gas sensing device for detecting the concentration of a selected gaseous constituent, in a carrier gas stream, the combination comprising:

(a) an ion transporting membrane;

(b) catalytic sensing and reference electrodes positioned on one side of the membrane and a counter electrode positioned on the opposite side of said membrane;

(c) potentiostatic circuit means coupling sensing, reference and counter electrodes for maintaining the potential at the sensing electrode constant and for maintaining a fixed potential difference between sensing and reference electrodes by driving current between counter and sensing electrodes, said sensing electrode being maintained at a potential which makes the device insensitive to the carrier gas;

(d) an ionically conductive, low resistance path on one side of the membrane, said path extending between the counter electrode and an area which is spatially aligned with the reference electrode, said membrane having been treated to provide said low resistance path between the counter electrode and the area spatially aligned with said reference electrode;

(e) means for exposing the sensing electrodes to a carrier gas stream containing the constituent to be sensed;

(f) means for flooding the counter electrode side of the membrane with water to produce water transport in the vapor phase across said membrane to the sensing electrode to humidify the gas stream brought to the sensing electrode;

(g) means for measuring the current which flows between the counter and sensing electrodes to maintain the sensing electrode potential constant, said current being a measure of the gas concentration.

* * * * *